(12) United States Patent
Abe et al.

(10) Patent No.: US 8,577,105 B2
(45) Date of Patent: Nov. 5, 2013

(54) ULTRASOUND DIAGNOSTIC APPARATUS AND METHOD OF DISPLAYING AN ULTRASOUND IMAGE

(75) Inventors: Yayoi Abe, Tokyo (JP); Masafumi Ogasawara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 141 days.

(21) Appl. No.: 13/111,308

(22) Filed: May 19, 2011

(65) Prior Publication Data

US 2011/0288415 A1 Nov. 24, 2011
US 2012/0150037 A9 Jun. 14, 2012

(30) Foreign Application Priority Data

May 19, 2010 (JP) ................................ 2010-115092

(51) Int. Cl.
*G06K 9/00* (2006.01)
(52) U.S. Cl.
USPC ........... 382/128; 382/130; 382/131; 600/437; 600/443; 600/458; 600/461
(58) Field of Classification Search
USPC .......... 600/437, 443, 458, 461; 382/128, 130, 382/131
See application file for complete search history.

(56) References Cited

U.S. PATENT DOCUMENTS

| | | | |
|---|---|---|---|
| 6,733,458 B1* | 5/2004 | Steins et al. .................. | 600/461 |
| 2002/0133098 A1* | 9/2002 | Shechtman et al. .......... | 600/594 |
| 2004/0106869 A1* | 6/2004 | Tepper .......................... | 600/443 |
| 2004/0234113 A1* | 11/2004 | Miga ............................. | 382/128 |
| 2006/0184019 A1 | 8/2006 | Ito et al. | |
| 2009/0030322 A1 | 1/2009 | Fujiwara et al. | |
| 2012/0330635 A1* | 12/2012 | Miga et al. ..................... | 703/11 |

FOREIGN PATENT DOCUMENTS

JP 10-151131 6/1998

\* cited by examiner

Primary Examiner — Baisakhi Roy
(74) *Attorney, Agent, or Firm* — Armstrong Teasdale LLP (57) ABSTRACT

An ultrasound diagnostic apparatus includes an ultrasound probe, a location sensor that detects a location of the ultrasound probe, and a location calculation device configured to calculate a location of echo data in a first three-dimensional coordinate system having a certain point as an origin based on the probe location. A deformation calculation device performs a deformation calculation to deform a shape of the body tissue in either an ultrasound image or a medical image captured by a medical imaging apparatus other than the ultrasound diagnostic apparatus to a shape of the body tissue of the other image. A display image control device performs a coordinate conversion between the coordinate system of the ultrasound image and a coordinate system of the medical image and displays a deformed image based on the deformation calculation and the other image about a same cross-section on a display device.

15 Claims, 9 Drawing Sheets

ULTRASOUND DIAGNOSTIC APPARATUS AND METHOD OF DISPLAYING AN ULTRASOUND IMAGE

CROSS REFERENCE TO RELATED APPLICATIONS

This application claims the benefit of Japanese Patent Application No. 2010-115092 filed May 19, 2010, which is hereby incorporated by reference in its entirety.

BACKGROUND OF THE INVENTION

The embodiments described herein relate generally to an ultrasound diagnostic apparatus displaying ultrasound images and medical images other than the ultrasound images.

A conventional ultrasound diagnostic apparatus transmits ultrasound waves to a subject by touching an ultrasound probe on the body surface of the subject and generates and displays an ultrasound image based on the acquired echo data. Examples of medical images other than the ultrasound images include an MRI (Magnetic Resonance Imaging) image and an X-ray CT (Computed Tomography) image. Japan Unexamined Patent Application No. 10-151131 discloses an ultrasound diagnostic apparatus that displays an ultrasound image and an MRI image or an ultrasound image and a CT image side-by-side.

When an ultrasound image and a medical image other than the ultrasound image about the same cross-section are displayed in the ultrasound diagnostic apparatus, shapes of the body tissue in each image may be different despite the same cross-section due to different postures at capturing an image. For example, when a breast is imaged by the ultrasound diagnostic apparatus, it is imaged in the supine position. On the other hand, when a breast is imaged by the MRI apparatus, it is imaged in the prone position. Thus, the breast in the ultrasound image appears squashed by its weight, and the breast in the MRI image hangs by gravity so that each shape in respective images is different.

Because of this, in the case displaying the ultrasound image and the medical image other than the ultrasound image together, it is desirable to display images showing identical shapes of the body tissue about the same cross-section for diagnosis.

BRIEF DESCRIPTION OF THE INVENTION

A first aspect of the invention is an ultrasound diagnostic apparatus including an ultrasound probe transmitting ultrasound waves to a subject and receiving an echo; a location sensor for detecting a location of the ultrasound probe; a location calculation device calculating a location of the echo data at a coordinate system in a three-dimension space with a certain point as an origin based on information detected by the location sensor; a deformation calculation device for performing a deformation calculation to deform a shape of the body tissue in either an ultrasound image based on the echo data or a medical image captured in advance by a medical imaging apparatus other than an ultrasound diagnostic apparatus to a shape of a body tissue of the other image; and a display image control device for performing a coordinate conversion between the coordinate system of an ultrasound image which is in the coordinate system of the three-dimensional space and a coordinate system of the medical image, and for displaying a deformed image based on the data acquired by the deformation calculation device and the other image about the same cross-section on a display device.

In a second aspect of the invention according to the first aspect, the deformation calculation device performs a deformation calculation using the particle method or the finite element method.

In a third aspect of the invention according to the second aspect, the deformation calculation device performs a deformation calculation assuming a stress on a body tissue in the other image based on the one image.

In a fourth aspect of the invention according to the ultrasound diagnostic apparatus according to any of preceding aspects, the body tissue is a breast.

In a fifth aspect of the invention according to the fourth aspect, the deformation calculation device performs a deformation calculation by the particle method or the finite element method on assumption that an uncompressed-hyperelastic body formed on a rigid body is a breast.

In a sixth aspect of the invention according to the fifth aspect, the deformation calculation device performs a deformation calculation using the particle method or the finite element method on assumption that a breast in the ultrasound image and the medical image is one of an uncompressed-hyperelastic body provided on lower surface of a rigid body in a horizontal position, an uncompressed-hyperelastic body provided on upper surface of a rigid body in a horizontal position, or an uncompressed-hyperelastic body provided on one surface of a rigid body in a vertical position.

In a seventh aspect of the invention according to the sixth aspect, the deformation calculation device performs a deformation calculation using the particle method or the finite element method on assumption that a breast in the ultrasound image is an uncompressed-hyperelastic body provided on upper surface of a rigid body in a horizontal position or an uncompressed-hyperelastic body provided on one surface of a rigid body in a vertical position, and a breast in the medical image is an uncompressed-hyperelastic body provided on lower surface of a rigid body in a horizontal position.

In an eighth aspect of the invention according to any of preceding aspects, the deformation calculation device performs a deformation calculation for deforming a shape of a body tissue in the ultrasound image to a shape of a body tissue in the medical image.

In a ninth aspect of the invention according to any of preceding aspects, the display image control device converts the echo data by a scan conversion to generate an ultrasound image.

A tenth aspect of the invention is the ultrasound diagnostic apparatus of ninth aspect, wherein a target of the deformation calculation is the echo data before scan conversion by the scan converter or an ultrasound image data after scan conversion by the scan converter.

In an eleventh aspect of the invention according to any of aspect of the first through seventh aspects, the deformation calculation device performs a deformation calculation for deforming a shape of a body tissue in the medical image to a shape of a body tissue in the ultrasound image.

In a twelfth aspect of the invention according to any of preceding aspects, further including a memory for storing the medical image data.

In a thirteenth aspect of the invention according to the twelfth aspect, the ultrasound image is an image in real time and the medical image is an image based on the data stored in the memory.

In a fourteenth aspect of the invention according to the twelfth aspect, the ultrasound image is an image based on data captured and stored in advance by transmitting/receiving ultrasound waves by the ultrasound probe, and the medical image is an image based on the data stored in the memory.

In a fifteenth aspect of the invention according to any of preceding aspects, the display image control device displays the deformed image and the other image side-by-side on the display device.

In a sixteenth aspect of the invention according to any of preceding aspects, wherein the display image control device displays the deformed image overlaid on the other image overlaid on the display device.

According to the embodiments in the above-mentioned aspects, deformed images are generated by performing a deformation calculation to deform a shape of the body tissue in any one of the ultrasound image and the medical image to a shape of the body tissue in the other image. Then, coordinate conversion between a coordinate system of the ultrasound image and a coordinate system of the medical image is performed, and the deformed image and the other image about the same cross-section are displayed. Because of this, the ultrasound image and the medical image displaying identical shapes of the body tissue at the same cross-section can be displayed.

Further, for example, even if the shape of the body tissue in both images are different due to the postures of the subject when capturing the ultrasound image and the medical image, the shape after deformation of the body tissue can be calculated by performing a deformation calculation using the particle method or the finite element method.

Further objects and advantages of the present invention will be apparent from the following description of the preferred embodiments of the invention as illustrated in the accompanying drawings.

DETAILED DESCRIPTION OF THE INVENTION

Embodiments of the invention will be explained.

First Embodiment

First of all, a first embodiment is explained based on FIG. 1 through FIG. 7. An ultrasound diagnostic apparatus 1 shown in FIG. 1 includes an ultrasound probe 2, a transmitting/receiving device 3, an echo data processing device 4, a display control device 5, a display device 6, an operation device 7, a control device 8, a HDD (Hard Disk Driver) 9, a magnetic field generation device 10, and a magnetic sensor 11.

Figure 1:
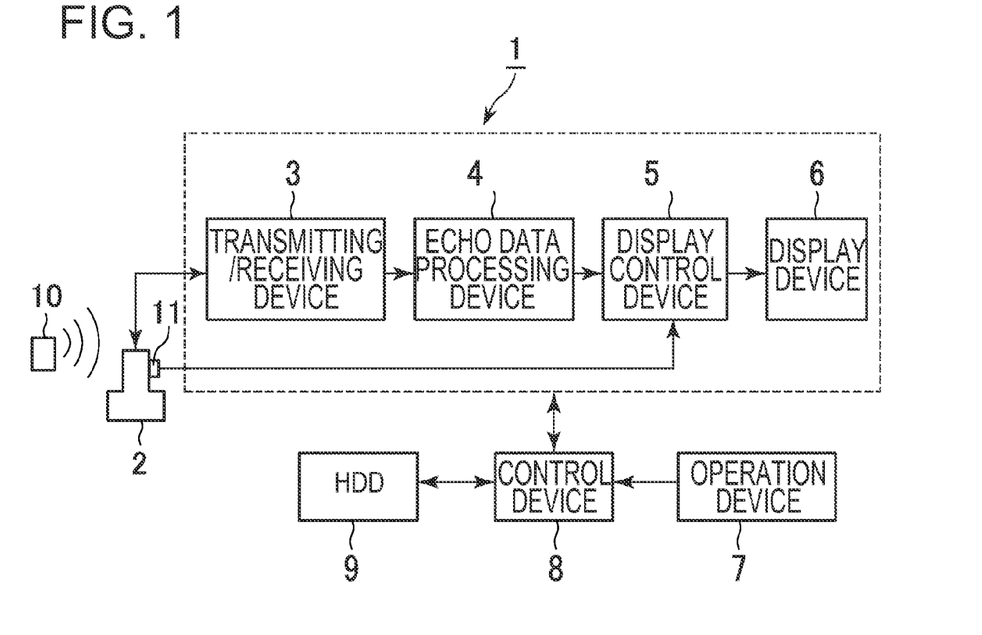
FIG. 1 is a block diagram showing one example of a schematic configuration of an embodiment of an ultrasound diagnostic apparatus.

The ultrasound probe 2 is configured with an array of ultrasound transducers (not shown), and the ultrasound transducers transmit ultrasound waves to a subject and receive its echo signal.

The magnetic sensor 11 includes hall elements and is provided on the ultrasound probe 2, for example. Magnetic field generated from the magnetic field generation device 10 including a magnetic field generation coil is detected by the magnetic sensor 11. The signal detected at the magnetic sensor 11 is input to the display control device 5. The signal by the magnetic sensor 11 can be input to the display control device 5 via a cable that is not illustrated, or can be input without wires. The magnetic field generation device 10 and the magnetic sensor 11 are examples of embodiments of a positioning sensor.

The transmitting/receiving device 3 activates the ultrasound probe 2 at a certain transmitting condition and makes the ultrasound beam scan a scan plane in line-serial procedure. The transmitting/receiving device 3 activates the ultrasound probe 2 by a control signal from the control device 8.

The transmitting/receiving device 3 performs a signal processing, such as phasing/adding process for the acquired echo signal by the ultrasound probe 2, and then outputs the processed echo data to the echo data processing device 4.

The echo data processing device 4 performs a predetermined process, such as a logarithmic compression process or an envelope demodulation process, to the echo data output from the transmitting/receiving device 3.

Figure 2:
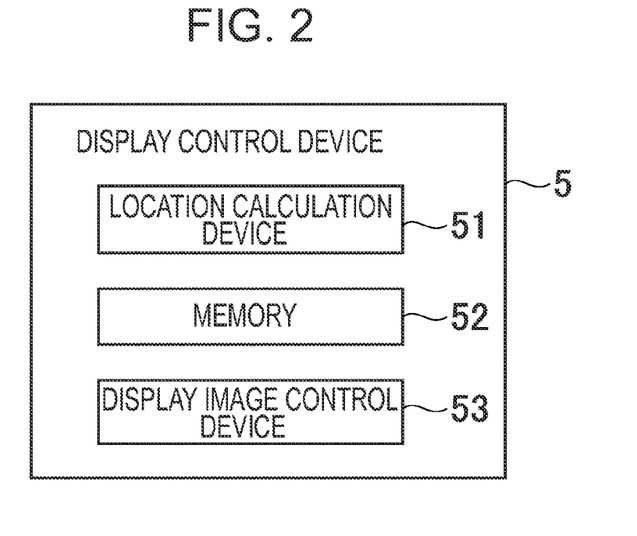
FIG. 2 is a block diagram showing the configuration of a display control device in the ultrasound diagnostic apparatus shown in FIG. 1.

The display control device 5 has a location calculation device 51, a memory 52, and a display image control device 53. The location calculation device 51 calculates information of the location and the tilt of the ultrasound probe 2 (herein after it is referred as "probe location information") in a space of three dimensions with the origin of the magnetic field generation device 10 based on a magnetic field detection signal from the magnetic sensor 11. Further, the location calculation device 51 calculates the location information of an echo data in the space of three dimensions based on the probe location information. A coordination system with their origin at the magnetic field generation device 10 is one example of embodiments of the coordination system of the ultrasound image. Also the location calculation device 51 is one example of embodiments of the location calculation device.

The memory 52 includes a semiconductor memory, such as RAM (Random Access Memory) or ROM (Read Only Memory). For example, the echo data output from the echo data processing device 4, which will be converted to the ultrasound image data in the display image control device 53, which will be discussed later, is stored in the memory 52. The data before being converted to the ultrasound image data is referred as raw data. The raw data can be stored in the HDD 9.

The medical image data captured by a medical imaging apparatus other than the ultrasound diagnostic apparatus 1 is stored in the memory 52 or the HDD 9, as explained later. The memory 52 and the HDD 9 are examples of embodiments of a memory device.

The display image control device 53 performs scan conversion by a scan converter from the echo data output from the echo data processing device 4 to the ultrasound image data. Then, the display image control device 53 displays the ultrasound image (B-mode image) on the display device 6 based on the ultrasound image data.

The display image control device 53 performs a coordinate conversion between the coordination system of the ultrasound image and the coordination system of the medical image other than the ultrasound image and displays both the ultrasound image and the medical image of the same cross-section on the display device 6. In this embodiment, as explained later, the ultrasound image and the medical image are displayed side-by-side on the display device 6.

As explained later, the medical image in this embodiment is an MRI image. The MRI image displayed on the display device 6 is a deformed MRI image acquired in a deformation calculation device 81, which will be explained later. The details will be explained later. The display image control device 53 is one example of embodiments of a display image device.

The display device 6 includes a LCD (Liquid Crystal Display) or a CRT (Cathode Ray Tube). The operation device 7 includes a keyboard and a pointing device (not illustrated) for an operator to command or input information.

The control device 8 includes a CPU (Central Processing Unit). The control device 8 reads out the control program stored in the HDD 9 and executes functions at respective devices in the ultrasound diagnostic apparatus 1.

Figure 3:
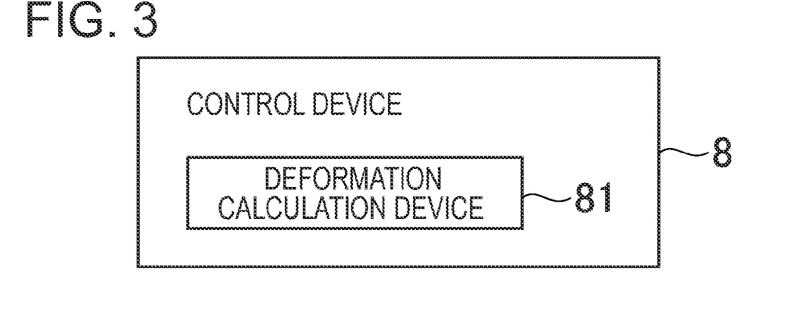
FIG. 3 is a block diagram showing the configuration of a control device in the ultrasound diagnostic apparatus shown in FIG. 1.

The control device 8 includes a deformation calculation device 81 as shown in FIG. 3. The deformation calculation device 81 performs a deformation calculation for deforming a shape of the body tissue in either one of the ultrasound image or the MRI image to a shape of the body tissue of the other image. In this embodiment, the deformation calculation device 81 performs a deformation calculation for deforming the shape of a breast in the MRI image to the shape of a breast in the ultrasound image. The deformation calculation device 81 is one example of embodiments of a deformation calculation device.

Figure 4:
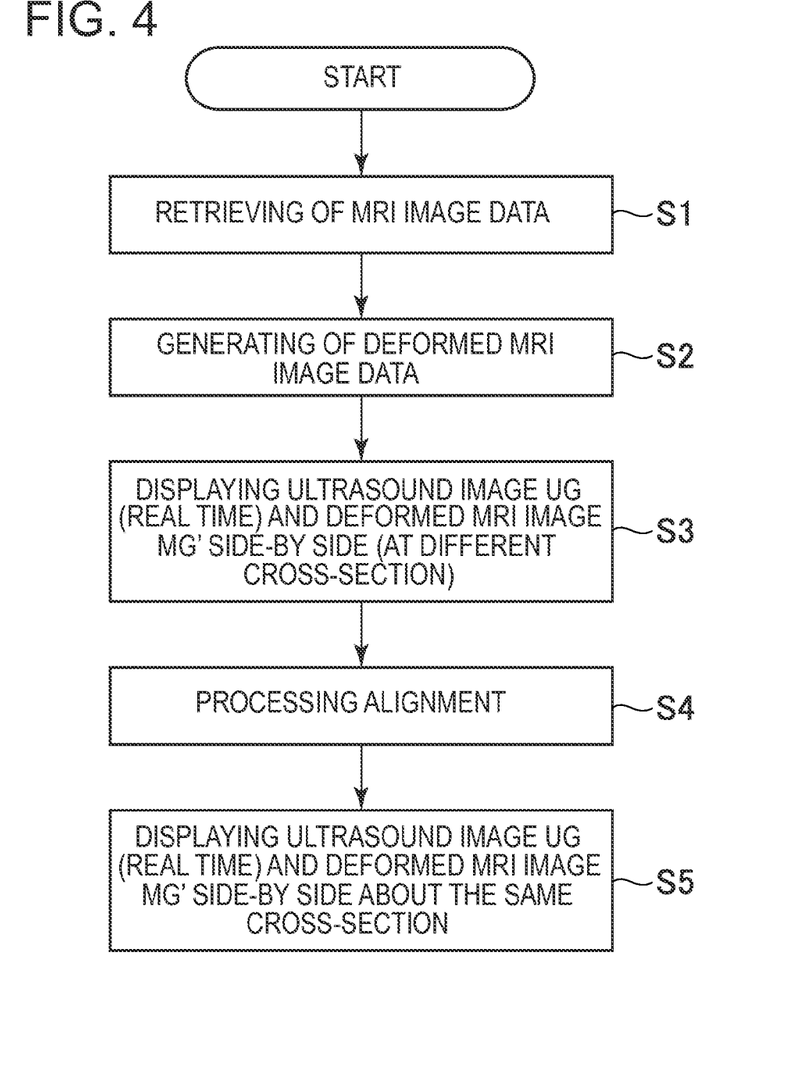
FIG. 4 is a flow chart showing a process of the ultrasound diagnostic apparatus of the first embodiment.

Now an operation of the ultrasound diagnostic apparatus 1 is explained based on a flow chart shown in FIG. 4. First, in step S1, the ultrasound diagnostic apparatus 1 takes the MRI image data captured by an MRI apparatus that is not illustrated. The MRI image data taken in the ultrasound diagnostic apparatus 1 is stored in the memory 52 or the HDD 9.

Figure 5A:
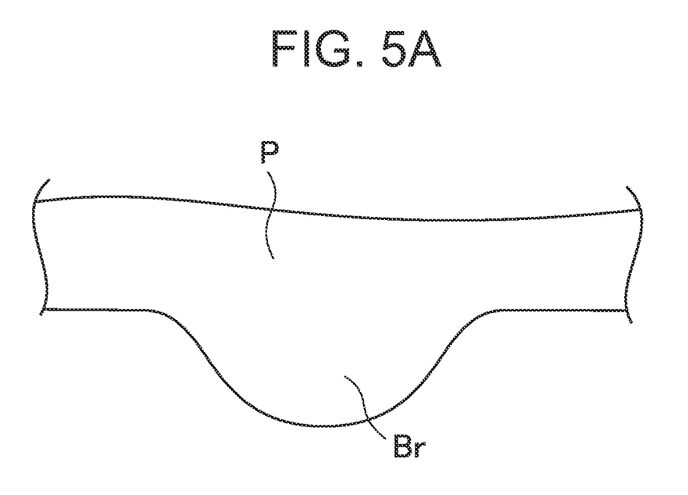
FIG. 5A shows a shape of a breast at capturing an image by an MRI apparatus.
Figure 5B:
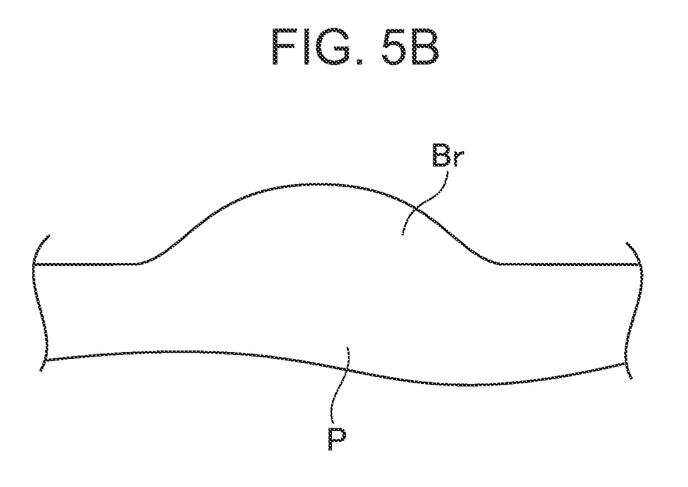
FIG. 5B shows a shape of a breast at capturing an image by an ultrasound diagnostic apparatus.

Here, a target body tissue for capturing image is a breast. When a breast is imaged by the MRI apparatus, a subject P is in the prone position so that the breast Br hangs as shown in FIG. 5A. On the other hand, as mentioned later, when a breast is imaged by ultrasound diagnostic apparatus, the subject P is in the supine position so that the breast Br is in a shape as if it is squashed by its weight as shown in FIG. 5B.

Next in step S2, the deformation calculation device 81 performs a deformation calculation to the MRI image data and generates the MRI image data that is deformed. In particular, the deformation calculation device 81 performs a deformation calculation for deforming the shape of the breast in the MRI image to the shape of the breast in the ultrasound image using the particle method or the finite element method. These methods are used for deformation analysis of an object. Thus, in this embodiment, the MRI image is one example of embodiments of one image, and the ultrasound image is one example of embodiments of the other image.

Here, it is a condition that the breast sits over the pectoralis major muscle in the human body, so when a deformation calculation of the shape of breast is performed by the particle method or the finite element method, a model that the pectoralis major muscle is a rigid body and the breast is an uncompressed-hyperelastic body is assumed. That is, the deformation of the shape of the uncompressed-hyperelastic body set on the rigid body is calculated by the particle method or the finite element method.

Figure 6A:
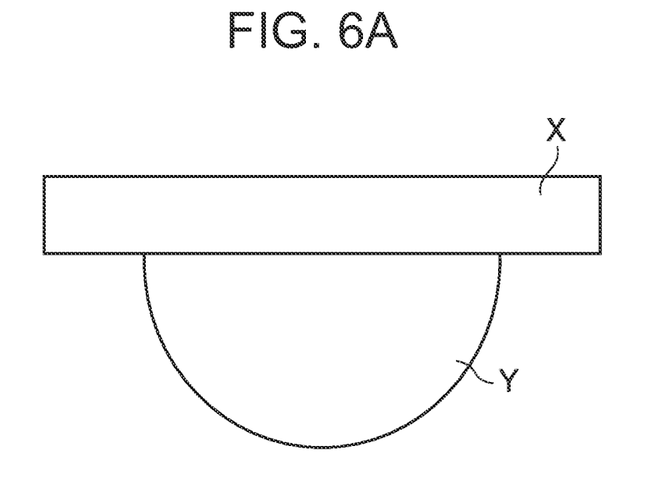
FIG. 6A shows a condition that an uncompressed-hyperelastic body hangs down from the lower surface of a rigid body.
Figure 6B:
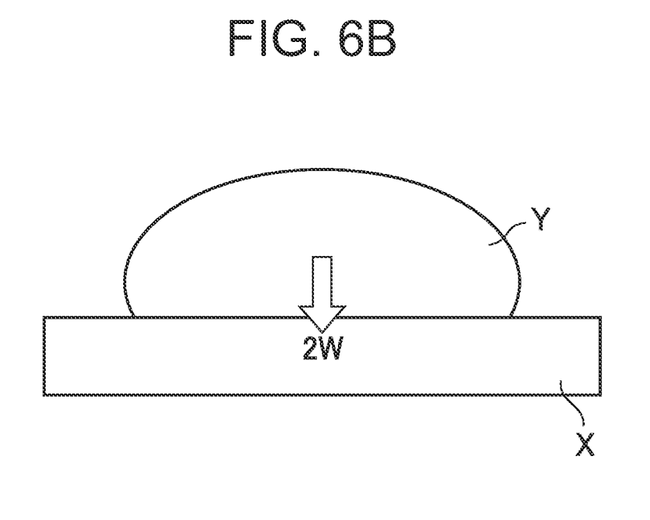
FIG. 6B shows a condition that an uncompressed-hyperelastic body is pressed by its weight to the upper surface of a rigid body.

For more detail, the posture at capture of an image of the subject by the MRI apparatus is the prone position. Therefore, as the breast in the MRI image, it is assumed that the uncompressed-hyperelastic body Y sets on the lower surface of the rigid body X that is in a horizontal position hangs down as shown in FIG. 6A. On the other hand, the posture at capture of an image of the subject by the ultrasound diagnostic apparatus is the supine position. Therefore, as the breast in the ultrasound image, it is assumed that the uncompressed-hyperelastic body Y sets on the lower surface of the rigid body X which is in a horizontal position is pressed by its weight as shown in FIG. 6B. The particle method or the finite element method calculates the deformation shape of the uncompressed-hyperelastic body Y changing from the condition that the uncompressed-hyperelastic body Y hangs down from the lower surface of rigid body X as shown in FIG. 6A to the condition that the uncompressed-hyperelastic body Y is pressed by its weight to the upper surface of the rigid body. That is, the method calculates to change the shape of the breast in the MRI image to the shape of the breast in the ultrasound image.

By the calculation of the deformation of the shape with the particle method or the finite element method, as shown in FIG. 6A, deformed shape of the uncompressed-hyperelastic body Y accompanying the stress change is evaluated in the case that the condition that the uncompressed-hyperelastic body Y hangs from the lower surface of the rigid body X is changed to the condition that it is pressed by its weight to the upper surface of the rigid body X. In such deformation calculation with the particle method or the finite element method, the size and direction of relative stress to the uncompressed-hyperelastic body Y in FIG. 6B is considered under the condition that the condition shown in FIG. 6A is the initial state. Concretely, in FIG. 6B with the condition of FIG. 6A as a standard, the stress F=2W that is two times of gravity (volume force) W is acted to the uncompressed-hyperelastic body Y in a downward direction (a direction that the upper surface of the rigid body X receive the stress in FIG. 6B). Note that the gravity used herein is a relative gravity when the condition of FIG. 6A is a standard.

The deformed MRI image data acquired by the deformation calculation is stored in the memory 52 or the HDD 9.

Next in step S3, ultrasound waves are transmitted to the subject in the supine position by the ultrasound probe 2 and the echo is received. Then, the display image control device 53 displays the ultrasound image UG at real time about transmitting/receiving surfaces on the display device 6. Further, the display image control device 53 displays on the display device 6 the deformed MRI image MG' about an arbitrary cross-section and the ultrasound image UG side-by-side based on the deformed MRI image data. Here, only deformed MRI image MG' of the cross-section which is different from the ultrasound image UG is displayed. In fact, the deformed MRI image MG' is an image that the subject P is in the supine position (the condition shown in FIG. 5B).

Next in step S4, an alignment process of the coordinate system of the ultrasound image UG and the coordinate system of the deformed MRI image MG' is performed. Concretely, an operator moves either one of or both of the cross-section(s) of the ultrasound image UG and the deformed MRI image MG' comparing the images displayed on the display device 6, and displays the ultrasound image UG and the deformed MRI image MG' of the same cross-section. The shifting of the cross-section of the ultrasound image UG is performed by changing a position of the ultrasound probe 2. The shifting of the cross-section of the deformed MRI image is performed by controlling the operation device 7 to command the change of the cross-section.

Whether the cross-sections are the same or not is determined by the operator by referring characteristic regions. In fact, the scan plane of ultrasound waves by the ultrasound probe 2 is parallel to the sliced surface of the MRI image.

After the ultrasound image UG and the deformed MRI image MG' about the same cross-section are displayed, the operator inputs a command that the same cross-section are displayed. Because of this, a coordinate conversion of the coordinate system of the ultrasound image UG and of the deformed MRI image MG' are allowed and the alignment process is completed.

Figure 7:
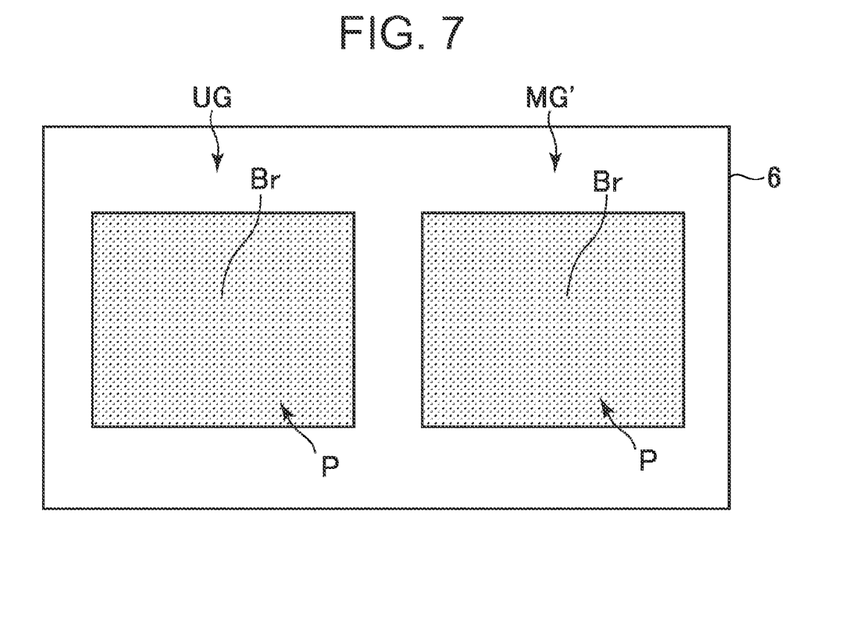
FIG. 7 shows a display device where an ultrasound image and a deformed MRI image at the same cross-section are displayed side-by-side.

In step S5 after completing the alignment process in the step S4, as shown in FIG. 7, the display image control device 53 displays on the display device 6 the deformed MRI image MG' of the same cross-section of the scan plane of the ultrasound waves by the ultrasound probe 2 next to the ultrasound image UG of the scan plane. The display image control device 53 performs the coordinate conversion of the coordinate system of the ultrasound image UG and of the deformed MRI image MG' and displays the deformed MRI image MG' that is the same cross-section of the ultrasound image UG. Here is the explanation about the coordinate conversion by the display image control device 53: in this embodiment, the position information of the echo data which is the coordinate system of the ultrasound image UG is converted to the coordinate system of the deformed MRI image MG'. Then, the display image control device 53 displays the deformed MRI image MG' about the certain cross-section acquired from the coordinate conversion. Even if the scan plane of the ultrasound waves by the ultrasound probe 2 is changed, the display image control device 53 displays the deformed MRI image about a cross-section that is newly captured. Therefore, even if the ultrasound probe 2 is moved and the cross-section of the ultrasound image is changed, the deformed MRI image MG' about the same cross-section is newly captured.

According to the ultrasound diagnostic apparatus 1 of this embodiment, the ultrasound image UG and the deformed MRI image MG' are images of the subject P in the supine position, so the same images of the same shapes of the breast about the same cross-section can be displayed. Thus, it is advantageous for diagnosis.

Although the shape of the breast in the supine position and in the prone position is greatly different, the shape of the breast after deformation can be calculated because the deformation calculation of the shape of the breast is performed using the particle method or the finite element method.

Figure 8:
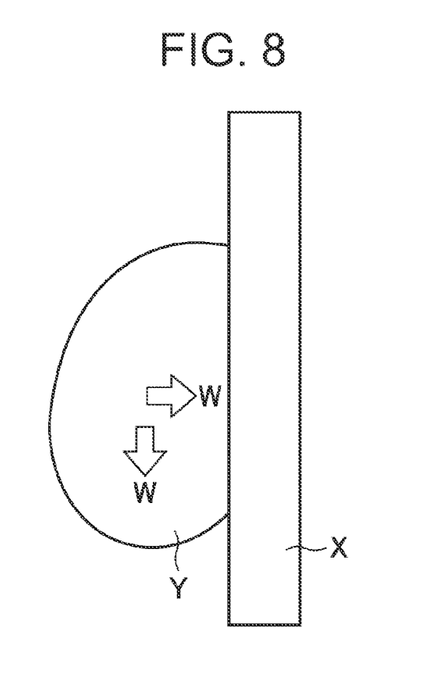
FIG. 8 explains a deformation calculation in alternative example of the first embodiment.

Next, an alternative example of the first embodiment is explained. In the foregoing embodiment, transmitting/receiving of ultrasound waves was performed to the subject in the supine position, but when it is performed to the subject in the standing position, it is assumed that the breast is the uncompressed-hyperelastic body Y sets on one surface of the rigid body X in a vertical position as shown in FIG. 8. Then, deformation of the uncompressed-hyperelastic body Y in the condition shown in FIG. 6A is changed to the condition shown in FIG. 8 is calculated by the particle method or the finite element method. In this case, as the stress for performing the deformation calculation, the stress of the condition shown in FIG. 8 is considered in a case that the condition shown in FIG. 6A is an initial condition. That is, as the stress, the gravity (volume force) W in vertically-downward direction (a direction parallel to the rigid body X in FIG. 8) and the gravity (volume force) W in parallel direction to the rigid body X (a direction which is pressed to one surface of the rigid body X in FIG. 8) are considered. Also, note that the gravity used herein is a relative gravity when the condition of FIG. 6A is a standard.

Second Embodiment

Next, a second embodiment will be explained. In the foregoing first embodiment, the real-time ultrasound image UG and the deformed MRI image having the same cross-section of the ultrasound image UG are displayed. However, in the second embodiment, the deformation calculation is performed with raw data stored in the HDD 9 or the memory 52 to generate deformed echo data. Then, the deformed ultrasound image UG' based on the deformed echo data and the MRI image MG based on the MRI image data are displayed on the display device 6.

Figure 9:
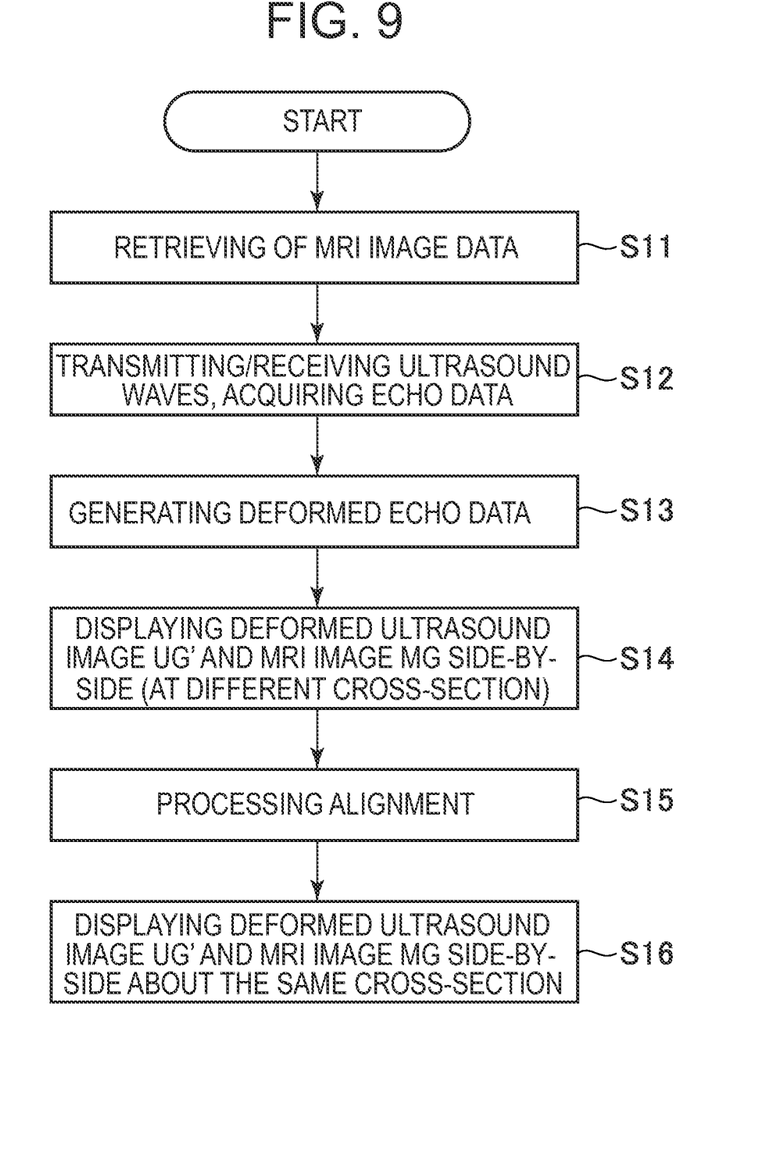
FIG. 9 is a flow chart showing a process in the ultrasound diagnostic apparatus of the second embodiment.

It is concretely explained on the basis of the flow chart in FIG. 9. In step S11 of FIG. 9, like the step S1 of the first embodiment, the MRI image data is taken to the ultrasound diagnostic apparatus 1 and stored in the memory 52 or the HDD 9.

Next in step S12, transmitting/receiving of the ultrasound waves to the subject by the ultrasound probe 2 is performed to capture the echo data. In this step S12, the ultrasound probe 2 scans the three-dimensional region to capture three-dimensional echo data (volume data). The captured echo data is stored in the memory 52 or the HDD 9 as raw data.

Next in step S13, the deformation calculation is performed by the deformation calculation device 81 for the three-dimensional echo data captured in the step S12 and the deformed echo data is generated. The deformation calculation is performed on respective cross-sections of the three-dimensional echo data.

Figure 10A:
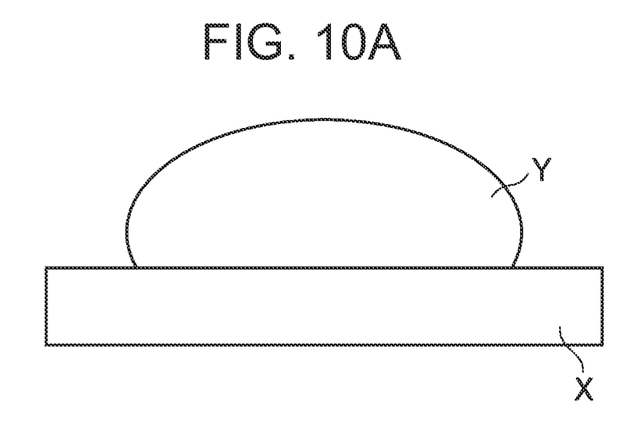
FIG. 10A shows a condition that an uncompressed-hyperelastic body is pressed by its weight to the upper surface of a rigid body.
Figure 10B:
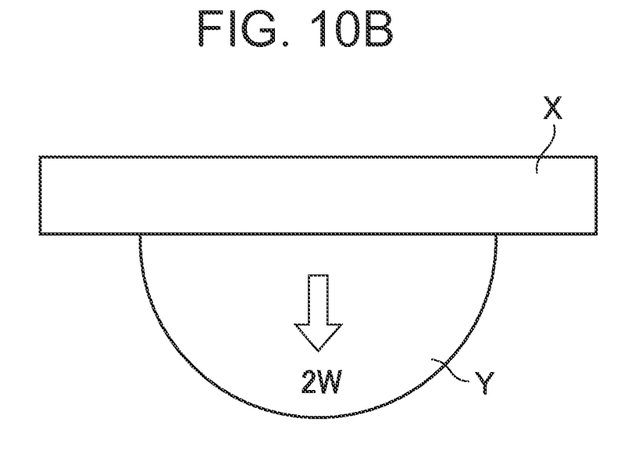
FIG. 10B shows a condition that an uncompressed-hyperelastic body hangs down from the lower surface of a rigid body.

In the deformation calculation in this step S13, it is assumed that the pectoralis major muscle is a rigid body and the breast is an uncompressed-hyperelastic body. And the deformation calculation using the particle method or the finite element method is performed to the deformation of the uncompressed-hyperelastic body. However in this embodiment, the deformation of the uncompressed-hyperelastic body Y in the case of change from the condition that the uncompressed-hyperelastic body Y is pressed by its weight to the upper surface of the rigid body, as shown in FIG. 10A to the condition that the uncompressed-hyperelastic body Y hangs down from the lower surface of rigid body X as shown in FIG. 10B by calculating with a particle method or a finite element method. Then, a calculation is performed to change the shape of the breast in the ultrasound image to the shape of the breast in the MRI image. In this embodiment, in the deformation calculation, the size and direction of the stress applied to the uncompressed-hyperelastic body Y in FIG. 10B is considered under the condition that the condition shown in FIG. 10A is an initial state. Concretely, in FIG. 10B with the condition of FIG. 10A as a standard, the stress F=2W that is two times of gravity (volume force) W is acted to the uncompressed-hyperelastic body Y in a vertical and downward direction (a direction that the upper surface of the rigid body X receive the stress in FIG. 10B). Note that the gravity used herein is a relative gravity when the condition of FIG. 10A is a standard.

The deformed echo data acquired by the deformation calculation is stored in the memory 52 or the HDD 9.

Next in step S14, the display image control 53 displays the deformed ultrasound image UG' based on the deformed echo data and the MRI image MG based on the MRI image data side-by-side. Here, the cross-sections of the deformed ultrasound image UG' and the MRI image MG are different. The deformed ultrasound image UG' is an image of the subject P in the prone position (position shown in FIG. 5A).

Next in step S15, the alignment process of the coordinate system of the deformed ultrasound image UG' and the coordinate system of the MRI image MG is performed. Particularly, this alignment process is the same as the process of the step S4 in the first embodiment and it is processed by comparing the deformed ultrasound image UG' and the MRI image MG displaying the same cross-section. In fact, the shifting of the cross-section of the deformed ultrasound image UG' is done by inputting a command to change the cross-section by operating the operation device 7 as it is done to the move of the cross-section of the MRI image.

Figure 11:
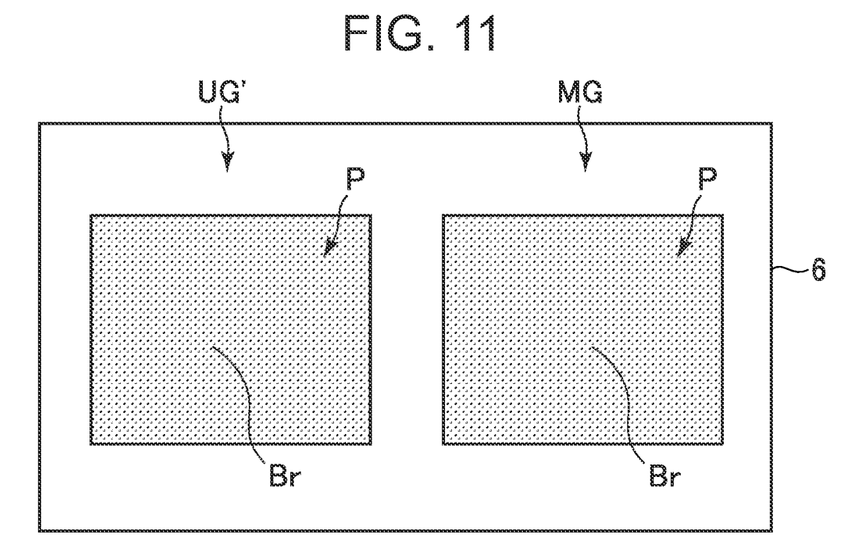
FIG. 11 shows a display device where an ultrasound image and a deformed MRI image about the same cross-section are displayed side-by-side in the second embodiment.

In step S16, after completing the alignment process in the step S15, the display image control device 53, as shown in FIG. 11, displays on the display device 6 the deformed ultrasound image UG' and the MRI image MG about the same cross-section. In this step S16, by the command from the operation device 7, even if either of the cross-sections of the deformed ultrasound image UG' and the MRI image MG is changed, the display image control device 53 converts the coordinate system of the image where the cross-section is changed to the coordinate system of the image where the cross-section is not changed so that the deformed ultrasound image UG' and the MRI image MG about the same cross-section are displayed. For example, when the cross-section of the deformed ultrasound image UG' is changed, a coordinate of newly acquired cross-section in the coordinate system of the deformed ultrasound image UG' is converted to the coordinate system of the MRI image MG, then the cross-section corresponding to the coordinate system of the MRI image MG is identified and the MRI image having the same cross-section as the renewed cross-section is displayed. Also, when the cross-section of the MRI image MG is changed, a coordinate of newly acquired cross-section in the coordinate system of the MRI image MG is converted to the coordinate system of the deformed ultrasound image UG', then the cross-section corresponding to the coordinate system of the deformed ultrasound image UG' is identified and the deformed ultrasound image UG' about the cross-section which is the same cross-section as the renewed cross-section is displayed.

According to the second embodiment described above, the deformed ultrasound image UG' and the MRI image MG are images of the subject P is in the prone position, so the same images of the same shapes of the breast about the same cross-section can be displayed, as in the first embodiment. Thus, it is advantageous for diagnosis.

In the second embodiment, instead of the ultrasound image, the deformed MRI image acquired by deforming the shape of the breast in the MRI image to the shape of breast in the ultrasound image, can be displayed with the ultrasound image.

The invention was explained with above-mentioned embodiments, but it will be understood that the invention can be modified in various ways without departing from the spirit and scope of the invention. For example, the medical image is not limited to the MRI image and an X-ray CT image or an image captured by mammography, for example, can be modified.

Further, in the second embodiment, instead of the deformation calculation subject to the raw data which is the echo data before scan conversion by a scan converter in the display image control device 53, the deformation calculation can be applied to the ultrasound image data after scan conversion.

Figure 12:
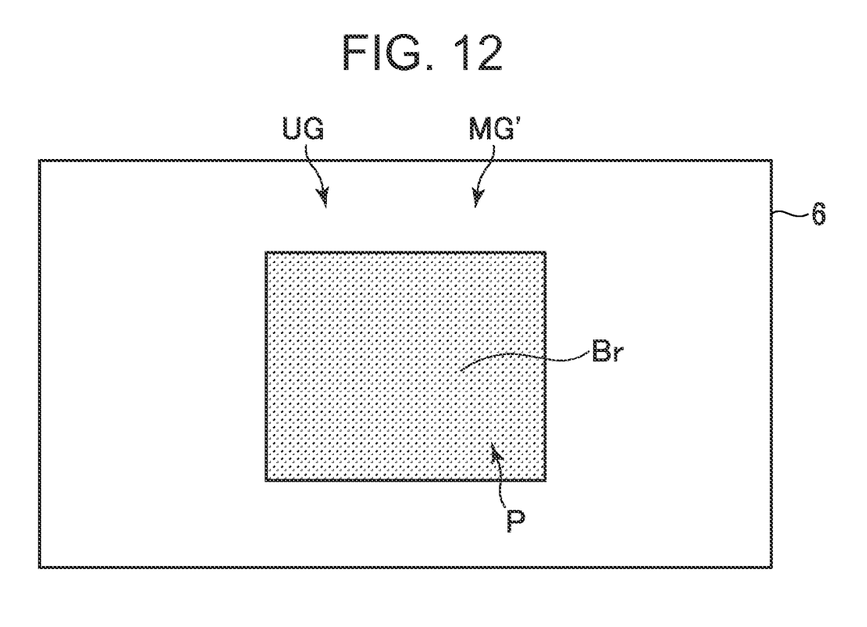
FIG. 12 shows a display device where ultrasound image and a deformed MRI image at the same cross-section are overlaid and displayed about the same cross-section.

In the step S5 of the first embodiment, the display image control device 53 displays the ultrasound image UG and the deformed MRI image MG' at the same cross-section side-by-side, but as shown in FIG. 12, the ultrasound image UG and the deformed MRI image MG' at the same cross-section can be overlaid (or synthesized) and displayed as transparent images.

Figure 13:
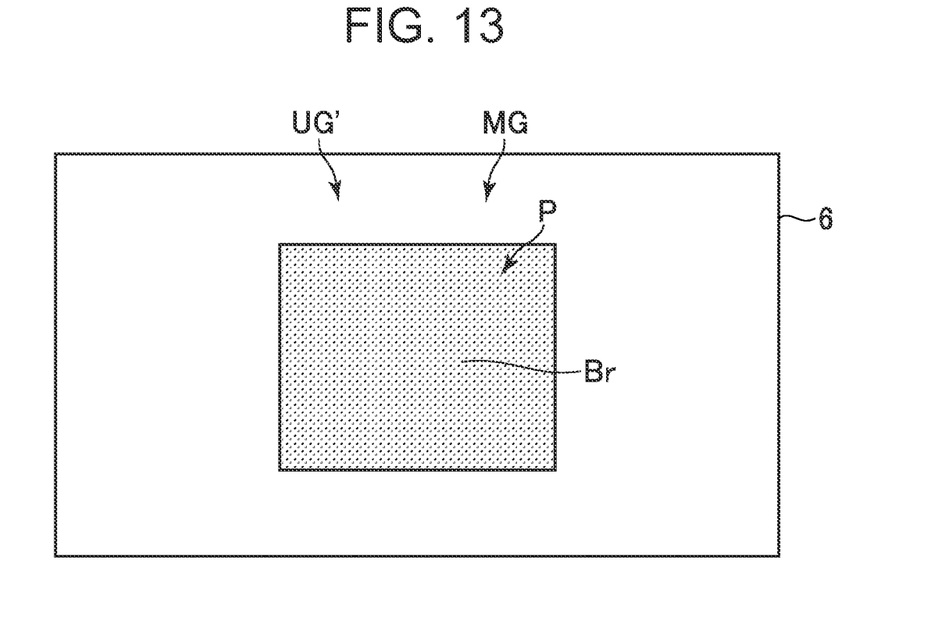
FIG. 13 shows a display device where a deformed ultrasound image and an MRI image at the same cross-section are overlaid and displayed about the same cross-section.

Similarly in step S16 of the second embodiment, the display image control device 53 displays the deformed ultrasound image UG' and the deformed MRI image MG at the same cross-section side-by-side, but as shown in FIG. 13, the deformed ultrasound image UG' and the deformed MRI image MG at the same cross-section can be overlaid (or synthesized) and displayed as transparent images.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasound diagnostic apparatus comprising:
   an ultrasound probe configured to transmit ultrasound waves to a subject and receive an echo, the subject including a breast;
   a location sensor configured to detect a location of the ultrasound probe;
   at least one processor configured to:
      calculate a location of echo data in a first coordinate system in a three-dimensional space having a certain point as an origin based on the probe location detected by the location sensor;
      perform a deformation calculation to deform a shape of the breast, in a first position, in a first image of an ultrasound image based on one of the echo data and a medical image captured in advance by a medical imaging apparatus other than the ultrasound diagnostic apparatus, to a shape of the breast in a second position, in a second image of one of the ultrasound image and the medical image, the ultrasound image having the first coordinate system, wherein each of the first position and the second position is one of a prone position, a supine position, and a standing position such that the first position is different than the second position;
      perform a coordinate conversion between the first coordinate system of the ultrasound image and a second coordinate system of the medical image; and display a deformed image based on the deformation calculation by the at least one processor and the second image about a same cross-section on a display device.

2. The ultrasound diagnostic apparatus of claim 1, wherein the at least one processor is configured to perform the deformation calculation using one of a particle method and a finite element method.

3. The ultrasound diagnostic apparatus of claim 2, wherein the at least one processor is configured to perform the deformation calculation assuming a stress acting on the breast in the second image based on the first image.

4. The ultrasound diagnostic apparatus of claim 1, wherein the at least one processor is configured to perform the deformation calculation by one of a particle method and a finite element method and the breast is an uncompressed-hyperelastic body formed on a rigid body.

5. The ultrasound diagnostic apparatus of claim 4, wherein the prone position includes an uncompressed-hyperelastic body provided on a lower surface of a rigid body in a horizontal position, the supine position includes the uncompressed-hyperelastic body provided on an upper surface of the rigid body in the horizontal position, and the standing position includes the uncompressed-hyperelastic body provided on one surface of the rigid body in a vertical position.

6. The ultrasound diagnostic apparatus of claim 5, wherein the breast in the ultrasound image is one of the uncompressed-hyperelastic body provided on the upper surface of the rigid body in the horizontal position and the uncompressed-hyperelastic body provided on the one surface of the rigid body in the vertical position, and the breast in the medical image is the uncompressed-hyperelastic body provided on the lower surface of the rigid body in the horizontal position.

7. The ultrasound diagnostic apparatus according to claim 1, wherein the at least one processor is configured to perform the deformation calculation to deform a shape of the breast in the ultrasound image to a shape of the breast in the medical image.

8. The ultrasound diagnostic apparatus according to claim 1, wherein the at least one processor is configured to covert the echo data by a scan conversion to generate the ultrasound image.

9. The ultrasound diagnostic apparatus of claim 8, wherein a target of the deformation calculation is one of the echo data before the scan conversion and ultrasound image data after the scan conversion.

10. The ultrasound diagnostic apparatus according to claim 1, wherein the at least one processor is configured to perform the deformation calculation to deform a shape of the breast in the medical image to a shape of the breast in the ultrasound image.

11. The ultrasound diagnostic apparatus according to claim 1, further comprising a memory configured to store medical image data.

12. The ultrasound diagnostic apparatus of claim 11, wherein the ultrasound image is an image in real time and the medical image is an image based on the data stored in the memory.

13. The ultrasound diagnostic apparatus of claim 11, wherein the ultrasound image is an image based on data captured and stored in advance by transmitting/receiving ultrasound waves using the ultrasound probe, and the medical image is an image based on the data stored in the memory.

14. The ultrasound diagnostic apparatus according to claim 1, wherein the at least one processor is configured to display the deformed image and the second image side-by-side on the display device.

15. The ultrasound diagnostic apparatus according to claim 1, wherein the at least one processor is configured to display the deformed image overlaid on the second image on the display device.

* * * * *